US005736126A

United States Patent [19]

Van Engelen et al.

[11] Patent Number: 5,736,126
[45] Date of Patent: Apr. 7, 1998

[54] LIQUID TRANSDERMAL ANALGESIC

[76] Inventors: H. Wayne Van Engelen; Patricia A. Van Engelen, both of 9618 Savannah Crossing Ct., Vienna, Va. 22182

[21] Appl. No.: 616,931

[22] Filed: Mar. 15, 1996

[51] Int. Cl.⁶ .............................. A61K 31/60; A61K 7/26
[52] U.S. Cl. ................................. 424/78.02; 424/78.06
[58] Field of Search ........................... 424/78.02, 78.06

[56] References Cited

U.S. PATENT DOCUMENTS

| | | | |
|---|---|---|---|
| 1,787,924 | 1/1931 | Whorton. | |
| 2,056,208 | 10/1936 | Putt | 167/65 |
| 2,095,571 | 10/1937 | Nichols | 167/62 |
| 2,542,897 | 2/1951 | Brown et al. | 424/78.02 |
| 3,119,739 | 1/1964 | Campbell | 167/58 |
| 4,665,063 | 5/1987 | Bar-Shalom | 514/164 |
| 4,948,588 | 8/1990 | Kamiya et al. | 424/436 |
| 4,975,269 | 12/1990 | Chavkin et al. | 424/45 |
| 5,034,221 | 7/1991 | Rosen et al. | 424/73 |
| 5,164,416 | 11/1992 | Nagai et al. | 514/763 |
| 5,198,217 | 3/1993 | Vedros | 424/195.1 |
| 5,223,267 | 6/1993 | Nichols | 424/489 |

*Primary Examiner*—Peter F. Kulkosky
*Attorney, Agent, or Firm*—Workman, Nydegger & Seeley

[57] ABSTRACT

A liquid composition applied transdermally for relief of pain comprises alcohol in an amount by weight of about 60 to about 93 percent; glycerine in an amount by weight of about 2 to about 14 percent; and an analgesic agent in an amount by weight of about 2 to about 28 percent. The use of aloe vera is an additional optional feature. The composition features transdermal pain relief such that a patient can apply an analgesic agent directly to an area of pain without the side effects such as stomach irritation which is normally associated with aspirin, for example. The composition may be sprayed or rolled directly onto the painful area. Because of the unique formula, the composition is safe to vital internal organs, requires no mixing before use, and is shelf stable for marketing purposes.

29 Claims, No Drawings

LIQUID TRANSDERMAL ANALGESIC

BACKGROUND OF THE INVENTION

1. The Field of the Invention

This invention is in the field of solutions which are applied topically for treatment of pain and irritation. Specifically, this invention relates to a liquid composition applied transdermally for relief of pain.

2. The Relevant Technology

The use of aspirin and other analgesic, anti-inflammatory agents is well known and has proven to be very valuable in the medical and scientific community. Aspirin has shown to have a variety of benefits in the treatment of aches and pains such as muscular aches, strains and cramps, arthritis, joint pain, lower back discomfort, bursitis, rheumatism, burns, insect bites and sports injuries.

However, certain side effects of aspirin, such as stomach irritation, may cause individuals to discontinue the use of this useful pain killer and anti-inflammatory. The ability to apply aspirin to an area of discomfort without ingesting the aspirin is a need which has been long felt within the medical community.

In addition, the ability to apply non-aspirin analgesics in an effective transdermal manner is a long-felt need. Applying an analgesic transdermally allows one to focus the analgesic in a certain painful area without diluting it by coursing it through the blood stream.

A variety of difficulties, however, are associated with the goal of achieving a safe and stable form of transdermal analgesic. First, it is vital that the analgesic permeate the necessary layers of skin in order to anesthetize pain without adversely affecting vital internal organs. Thus, it is critical to achieve a solution which dissolves aspirin or other analgesic agents and transports it topically to the area of pain.

Second, while certain solutions effectively cause analgesics to permeate skin, it is critical that the analgesic be stable within the solution such that it has a marketable shelf life. Aspirin is sparingly soluble in water. Permeating solutions may degrade aspirin and other analgesics by a variety of scientific processes including hydrolysis, glycolysis, and transesterification, for example. Until the present invention, teachings in the art indicated that aspirin was not stable in topical solutions involving the lower aliphatic alcohols because it too readily hydrolyzed to acidic and salicylic acids.

It would therefore be a significant advance in the art to discover and employ a composition having the ability to safely permeate skin, yet retain an analgesic such as aspirin in a shelf stable state.

SUMMARY AND OBJECTS OF THE INVENTION

Applicant has discovered that a composition of glycerin, alcohol, an analgesic agent, and optionally, aloe vera, sufficiently permeates the skin in order to effectively treat pain. Alcohol, preferably ethyl or isopropyl alcohol effectively dissolves the analgesic so that it can be absorbed through the skin. Glycerin, when employed in the proper percentages, acts as a stabilizer for the acetylsalicylic acid, triethanolamine salicylate or other analgesic agent such that the alcohol does not significantly affect the marketable shelf life of the composition. Glycerin also sufficiently disperses the analgesic agent such that the composition does not need to be shaken or stirred before topical use.

The invention comprises a liquid composition applied transdermally for relief of pain and includes alcohol in an amount of about 60 to about 93 percent by weight, glycerin in an amount by weight of about 2% to about 14% and an analgesic in an amount by weight of about 2% to about 28%. Optionally, aloe vera may be added in an amount by weight of about 0.3 to about 4%. The preferred analgesics are acetylsalicylic acid and triethanolamine salicylate.

Because of its liquid, well dispersed nature, the composition may be sprayed or rolled on the area where pain or aching exists without ingesting the composition. The resulting solution is an effective liquid topical analgesic and anti-inflammatory agent which does not disturb the digestive system and which is shelf stable for at least 18 months. The solution is effective for the relief of aches and pains associated with muscular aches, strains and cramps, arthritis, joint pain, burns, lower back discomfort, bursitis, rheumatism, insect bites, and sports injuries, athlete's foot, shingles, headaches, menstrual cramps, and tennis elbow.

An additional advantage of the topical solution is that the risk of overdose is dramatically decreased. Although the solution may provide four to six hours of pain relief and may permeate at least seven layers of skin to relieve pain, only negligible, microscopic amounts of the analgesic agent permeate into the blood stream, making overdose highly improbable.

Since the pain relieving solution is concentrated at the area where pain is indicating, the solution may be more effective than an oral dose, which is diluted in the body. In addition, the pain relief begins within a matter of minutes, or even within 60 to 90 seconds. Because of the unique composition, the solution need not be shaken or stirred before use and may be applied, for example, with a nonaerosal pump spray.

It is therefore an object of the present invention to provide a composition which exists in a liquid state and is applied transdermally for relief of pain which contains an analgesic, anti-inflammatory agent which is shelf stable.

It is a further object of the invention to provide such a solution which permeates the necessary layers of skin in order to address the aches and pains to be relieved but does not adversely affect the internal organs.

It is a further object of the invention to provide such a solution which can be applied directly in the area of pain on the body.

It is a further object of the invention to provide such a solution in a form which does not need to be shaken or stirred before use.

These and other objects and features of the present invention will become more fully apparent from the following description and appended claims, or may be learned by the practice of the invention as set forth hereinafter.

DETAILED DESCRIPTION OF THE PREFERRED EMBODIMENTS

The invention comprises a liquid composition applied transdermally for relief of pain and includes alcohol in an amount by weight of about 60% to about 93%, glycerin in an amount by weight of about 2% to about 14% and an analgesic in an amount by weight of about 2% to about 28%. Optionally, aloe vera may be added in an amount by weight of about 0.3% to about 4%.

The mixing instructions for the formula are relatively simple. In one embodiment, in the percentages described below in Formulas 1 through 8, alcohol, glycerin, an analgesic agent, and optionally, aloe vera are mixed together until dissolved. The mixing in each embodiment is preferably carried out at a high speed in a stainless steel container. In another embodiment, in the percentages described below in FIGS. 1 through 8, alcohol is first mixed with the analgesic agent, such as aspirin, for about 20 minutes, after which glycerin is added and mixed for about 10 minutes, after which aloe vera is added, if desired, and mixed for about 30 minutes. In another embodiment, in the percentages described below in FIGS. 1 through 8, alcohol is mixed with glycerin for approximately 10 minutes, after which the analgesic agent is added and mixed for approximately 30 minutes, after which aloe vera, if employed is added and mixed for about five to about fifteen minutes.

Alcohol is contained within the mixture because it readily dissolves the analgesic agent and assists in allowing the analgesic agent to permeate the skin. Alcohol acts a good solvent for aspirin and other analgesics. Applicant's formula has proven to permeate at least seven layers of skin. While isopropyl and ethyl alcohol are preferred, any alcohol having similar permeability and dissolution qualities may be employed in applicant's formula. Grade USP anhydrous alcohol is preferred. In the most preferred embodiment, a free, prescription grade of isopropyl alcohol is employed, which is approximately 99.8 percent pure.

Glycerin acts as a stabilizer, preventing the alcohol from deactivating the analgesic effect of the analgesic agent and allowing the analgesic to remain in solution such that the composition does not need to be shaken before use, even after months on the shelf.

Acetylsalicylic acid and triethanolamine salicylate are the preferred analgesics. These analgesic agents are powerful, proven pain killers and act as anti-inflammatories as well. However, it is possible that the analgesic agents would include, for example, acetylsalicylic acid, triethanolamine salicylate, ibuprofen, naprosyn, acetaminophen, and any other salicylates, such as methyl salicylate. When triethanolamine salicylate is employed, it is often added in higher quantities because of its weaker strength than aspirin. USP grades of acetylsalicylic acid, triethanolamine salicylate, and glycerine are preferred.

Aloe vera, another proven pain reliever, may be employed on an optional basis to increase the pain relieving qualities of the composition. If employed, it is preferably present in a pure gel state, although a tolerance to about 98% to about 100% purity is allowable.

A preferred method of use is to direct a spray of approximately 0.337 ml approximately one inch away from the skin at the location where pain is indicating, then spray three times liberally on the skin and massage in until dry. After sixty seconds, the process may be repeated, followed by another application sixty seconds later if necessary. These delayed reapplications are recommended in light of the fact that if one sprays all at once, the composition may not have sufficient time to permeate the skin and may run off. It is recommended that contact with mucous membranes is avoided.

The foregoing description, and the methods of use and manufacture illustrated above relate to each of the following formulas for the invention.

| Ingredient | Percent By Weight |
|---|---|
| Formula 1 | |
| Alcohol | about 60% to about 93% |
| Glycerin | about 2% to about 14% |
| Analgesic Agent | about 2% to about 28% |
| Aloe Vera (Optional) | about 0.3% to about 4% |
| Formula 2 | |
| Alcohol | about 70% to about 93% |
| Glycerin | about 2% to about 12% |
| Acetylsalicylic Acid | about 2% to about 18% |
| Formula 3 | |
| Isopropyl Alcohol | about 70% to about 93% |
| Glycerin | about 2% to about 8% |
| Acetylsalicylic Acid | about 3.5% to about 19% |
| Aloe Vera | about 0.5% to about 3% |
| Formula 4 | |
| Isopropyl Alcohol | about 87.99% |
| Glycerin | about 4.81% |
| Acetylsalicylic Acid | about 6.1% |
| Aloe Vera | about 1.1% |
| Formula 5 | |
| Isopropyl Alcohol | about 88.38% |
| Glycerin | about 4.81% |
| Acetylsalicylic Acid | about 5.71% |
| Aloe Vera | about 1.1% |
| Formula 6 | |
| Alcohol | about 60% to about 90% |
| Glycerin | about 2% to about 14% |
| Triethanolamine salicylate | about 8% to about 28% |
| Formula 7 | |
| Isopropyl Alcohol | about 62% to about 90% |
| Glycerin | about 2% to about 12% |
| Triethanolamine salicylate | about 7% to about 27% |
| Aloe Vera | about 0.3% to about 4% |
| Formula 8 | |
| Isopropyl Alcohol | about 81% |
| Glycerin | about 3% |
| Triethanolamine salicylate | about 15% |
| Aloe Vera | about 1% |

Formulas 1 though 8 each provide a composition which provides pain relief, yet avoids the gastric irritation associated with orally ingested aspirin. The formulas are capable of being applied topically and have at least a comparable pain relieving effect as orally ingested aspirin, yet avoid the gastric side effects associated with orally ingested aspirin. The formulas containing acetylsalicylic acid thus provide salicylic acid in the blood stream which is negligible compared to the amount of salicylic acid provided into the blood stream by orally ingested aspirin. Each formula disclosed herein is a composition which provides transdermal pain relief without a digestive side effect and without being shaken or stirred before use.

Each formula also provides a composition which may be applied directly to the skin surrounding a specific painful location in the body to relieve the pain. In addition, each of the formulas disclosed herein provide a composition which has an effective shelf life of at least eighteen months. Furthermore, the formulas will permeate at least seven layers of skin to relieve pain without a digestive side effect. When employing the formulas disclosed herein, the pain relief begins within about one to two minutes.

The following Examples 1 through 8 demonstrate the results of experiments employing a test solution comprising: isopropyl alcohol in an amount of about 88.38% by weight, glycerin in amount of about 4.81% by weight, acetylsalicylic acid in an amount of about 5.71% by weight and aloe vera in an amount of about 1.1% by weight ("test solution"), a representative sample of Formulas 1 through 8. These examples demonstrate the safety and usefulness of each of the formulas described herein.

EXAMPLE 1

Pharmacokinetics Study on Internal Drug Levels of Formula 5

The objective of the test was to determine whether topical application of the test solution is followed by a rise of venous blood salicylic acid in two healthy human subjects. Two male subjects, one non-smoker and one smoker, aged 26 and 29 years, and weighing 67 kg and 74 kg, respectively were studied as described below.

After insertion of an intravenous cannula (venflon 21 gauge) into an antecubital arm vein, a 20 ml blood sample was withdrawn. The cannula was kept patent with heparinized saline. At time zero six metered sprays of the test solution were applied to a 20 cm diameter area of the skin on the lower back. The sprays were separated by only three minutes. Further blood samples were taken at 1, 2, 3, 4, 5, 6, 8, and 10 hours after the topical application. The subjects were kept in a designated room in the Drug Control Centre and were allowed to eat and drink (no alcohol) adlibitum.

Blood samples were analyzed for salicylic acid. Blood samples were placed in a heparinized tubes and centrifuged to provide plasma samples. Aliquots were frozen at −70° C. for future analysis and one set was used for immediate analysis.

The plasma samples were analyzed by SIM GC-MS using developments of a GC method used by Rance et at, Pharm Pharmacol. 1975; 27:425–429, which is incorporated herein in its entirety by reference. The method was found to be sensitive with a detection limit of 10 micrograms/L (10 ng/ml).

Both subjects were found to have salicylic acid present in the plasma at time zero (10 ng/ml subject a, and 30 ng/ml subject b). Neither subject had any history or other evidence which would suggest liver disease. After application of the spray plasma levels rose in both subjects and in both cases the 10 hours values were higher than the 8 hour values.

The key values from the analysis were:

| Time: | 0 | 10 h |
| --- | --- | --- |
| Subject A: | 10 ng/ml | 40 ng/ml |
| Subject B: | 30 ng/ml | 300 ng/ml |

The highest blood level seen in the study of the test solution was 300 ng/ml 10 hours after topical administration of 210 mg of the test solution. The method used was so sensitive that baseline levels of salicylic acid were detected above zero. It is possible that this salicylic acid was derived from naturally occurring salicylates in fruits and vegetables.

Acetylsalicylic acid is rapidly hydrolyzed after absorption. The rising levels of salicylate in both subjects suggest that some of the acetylsalicylic acid applied topically was absorbed through the skin, and was hydrolyzed. The differences between the two subjects may have been due to a number of variables: skin permeability, skin blood flow, skin temperature, capacity for hydrolysis, rate of hepatic degradation of acetylsalicylic acid and renal clearance.

The absolute plasma levels were an order of magnitude lower than would have been expected after an oral dose. In this study 210 mg was applied topically. By comparison, however, when 300 mg of aspirin was taken orally by 10 subjects, the average plasma levels of salicylic acid were estimated to be 22, 26, 21, and 12 mg/ml at 1, 2, 4, and 7 hours respectively. Rance, et al, supra.

A comparison of these values shows that the levels seen after topical administration of the test solution were negligible compared to those seen after oral administration of aspirin. The dose used orally was 1.43 times higher than the dose used topically (six sprays) in the pilot study. However, the blood levels were 40,000 to 87,000 times higher after the oral dose than the dose used topically in the pilot study. The blood levels after the topical administration are therefore minuscule by comparison with blood levels after oral dosage (about 1/30,000).

It follows that the drug levels in organs distant from the skin would also be minuscule, and it is most improbable that there would be any digestive side effect which could be attributed to salicylic acid as a consequence of the topical administration of the test solution at the dosage and in the manner described.

EXAMPLE 2

Stabililty Study

The objective of the test was to determine whether topical application of the test solution has an appreciable change in stability. The test solution was placed in a plastic spray bottle at room temperature for six months. After six months, the data was indicative of that expected for a stabilized compound. There was no appreciable change or degradation during the six month period of any of the ingredients, and acetylsalicylic acid was found in the amount of approximately 5.71% after the six month period.

EXAMPLE 3

Testing After Prolonged Storage

The objective of the test was to determine whether topical application of the test solution has an appreciable change in stability and effectiveness. After storage of over six months in a plastic spray bottle at room temperature, the test solution was applied to the headache in the neck region of a 30 year old female. The test solution was found effective in dispelling the headache. No instability or lack of effectiveness was indicated.

In other tests by the inventors, a composition of the test solution prepared eighteen months previously by the inventors was proven to be stable and effective in relieving pain on human subjects. In light of the foregoing tests, it is likely that the solution is shelf stable for more than 2 years.

EXAMPLE 4

Testing for Relief of Pain Associated with Rheumatoid Arthritis

A woman diagnosed with rheumatoid arthritis who suffered from progressive joint dysfunction employed the test solution for one month in addition to an intake of NSAID, which she had taken for years on a daily basis. The result was that after employing the test solution her joints became less swollen, and she experienced significantly more hand mobility, wrist mobility and knee motion. She was able to maintain her daily routine in more comfort and sleep pain-free.

EXAMPLE 5

Testing for Relief of Pain Relating to Bursitis

A woman suffered with Bursitis in her right hip for 16 years. She received frequent cortisone injections with no relief. In 1993, she underwent surgery to remove the bursa, following which the pain returned. The pain was so severe she could not even put a sheet over her hip at night. After a subsequent surgery in 1994, the pain returned again. No pain relievers worked for her. After testing the test solution, continual improvement in pain relief was noticed. She can now sleep on her hip and walk long distances.

EXAMPLE 6

Clinical Trial

The test solution was employed by a physician to treat numerous painful conditions ranging from disc degeneration to muscular strains. The results were most impressive. Patients responded to the tests and received pain relief in a very satisfactory manner.

EXAMPLE 7

Testing for Relief of Post-Surgical Pain and Stomach Ulcers

A male who had been in a serious automobile accident and had undergone several back surgeries and was nevertheless in serious pain tested the test solution and found that he was able to decrease a daily dose of morphine necessary for pain relief by one half when he employed the composition. The secondary benefit was that his stomach was given substantial relief and his specialist agreed that a surgery would not be required to rectify severe stomach ulcers caused by the previous medication. All internal bleeding has stopped and he is almost completely free from stomach pain.

EXAMPLE 8

Testing for Bruised Extremity

After bruising her toe, which immediately became swollen and painful, a woman confirmed that the toe was broken. After applying the test solution and gently massaging it into the toe, the swelling became tolerable and she was able to wear a high-heeled shoe without any further discomfort.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A liquid composition applied transdermally for relief of pain, the composition comprising:
  alcohol in an amount by weight of about 60 to about 93 percent;
  glycerin in an amount by weight of about 2 to about 14 percent;
  an analgesic agent in an amount by weight of about 2 to about 28 percent, the analgesic agent comprising a derivative of salicylic acid; and
  aloe vera in an amount by weight of at least about 0.3 percent, the liquid composition permeating skin to relieve pain.

2. A composition as in claim 1, wherein aloe vera is in an amount by weight of about 0.3 to about 4 percent.

3. A composition as in claim 1, wherein the alcohol in an amount by weight of about 60 to about 93 percent is selected from the group consisting of isopropyl alcohol and ethyl alcohol.

4. A composition as in claim 1, wherein
  the alcohol is in an amount by weight of about 70 to about 93 percent;
  the glycerin is in an amount by weight of about 2 to about 12 percent; and
  the analgesic agent comprises acetylsalicylic acid, and is present in an amount by weight of about 2 to about 18 percent.

5. A composition as in claim 1, wherein
  the alcohol is isopropyl alcohol in an amount by weight of about 70 to about 93 percent;
  the glycerin is in an amount by weight of about 2 to about 8 percent; and
  the analgesic agent comprises acetylsalicylic acid in an amount by weight of about 3.5 to about 19 percent;
  wherein aloe vera is in an amount by weight of about 0.5 to about 3 percent.

6. A composition as in claim 1, wherein
  alcohol is in an amount by weight of about 60 to about 90 percent;
  glycerin is in an amount by weight of about 2 to about 14 percent; and
  the analgesic agent is triethanolamine salicylate, and is present in an amount by weight of about 8 to about 28 percent.

7. A composition as in claim 1, wherein
  the alcohol is isopropyl alcohol and is in an amount by weight of about 62 percent to about 90 percent;
  glycerin is in an amount by weight of about 2 to about 12 percent; and
  the analgesic agent comprises triethanolamine salicylate in an amount by weight of about 7 to about 27 percent; and wherein
  aloe vera is in an amount by weight of about 0.3 to about 4 percent.

8. A composition as in claim 7, wherein
  isopropyl alcohol is in an amount by weight of about 81 percent;
  glycerin is in an amount by weight of about 3 percent;
  triethanolamine salicylate is in an amount by weight of about 15 percent; and
  aloe vera is in an amount by weight of about 1 percent.

9. A composition as in claim 1, wherein the analgesic agent is selected from the group consisting of acetylsalicylic acid and triethanolamine salicylate.

10. A composition as in claim 1, wherein the analgesic agent comprises a salicylate.

11. A liquid composition applied transdermally for relief of pain, the composition comprising:
  isopropyl alcohol in an amount by weight of about 60 to about 93 percent;
  glycerin in an amount by weight of about 2 to about 14 percent;
  acetylsalicylic acid in an amount by weight of about 2 percent to about 28 percent; and
  aloe vera in an amount by weight of about 0.3 to about 4 percent, the liquid composition permeating skin to relieve pain.

12. A composition as in claim 11, wherein
  the isopropyl alcohol is in an amount by weight of about 87.99 percent;
  the glycerine is in an amount by weight of about 4.81 percent;

the acetylsalicylic acid is in an amount by weight of about 6.1 percent; and the aloe vera is in an amount by weight of about 1.1 percent.

13. A composition as in claim 11, wherein the isopropyl alcohol is in an amount by weight of about 70 to about 93 percent;

the glycerin is in an amount by weight of about 21 to about 8 percent;

the acetylsalicylic acid is in an amount by weight of about 3.5 to about 19 percent; and the aloe vera is in an amount by weight of about 0.5 to about 3 percent.

14. A method for making a liquid composition applied transdermally for relief of pain, comprising:

mixing alcohol in an amount by weight of about 60 to about 93 percent;

glycerin in an amount by weight of about 2 to about 14 percent;

an analgesic agent in an amount by weight of about 2 to about 28 percent, the analgesic agent comprising a derivative of salicylic acid; and aloe vera in an amount by weight of at least about 0.3 percent, the liquid composition permeating skin to relieve pain.

15. A method as in claim 14, wherein the analgesic agent is selected from the group consisting of acetylsalicylic acid, triethanolamine salicylate, and other salicylates; and the alcohol is selected from the group consisting of isopropyl alcohol and ethyl alcohol.

16. A method as in claim 14, wherein aloe vera is in an amount by weight of about 0.3 to about 4% of the composition.

17. A method as in claim 14, wherein the alcohol comprises isopropyl alcohol and is in an amount by weight of about 70 to about 93 percent;

glycerin is in an amount by weight of about 2 to about 8 percent; and the analgesic agent comprises acetylsalicylic acid in an amount by weight of about 3.5 to about 19 percent; and wherein aloe vera is in an amount by weight of about 0.5 to about 3 percent of the composition.

18. A method as in claim 17, wherein isopropyl alcohol is in an amount by weight of about 87.9 to about 88.4 percent;

glycerin is in an amount by weight of about 4.8 percent;

acetylsalicylic acid is in an amount by weight of about 5.7 percent to about 6.1 percent; and aloe vera is in an amount by weight of about 1.1 percent of the composition.

19. A method as in claim 14, wherein the alcohol is isopropyl alcohol in an amount by weight of about 62 percent to about 90 percent;

glycerin is in an amount by weight of about 2 to about 12 percent;

the analgesic agent is triethanolamine salicylate in an amount by weight of about 7 to about 27 percent; and aloe vera is in an amount by weight of about 0.3 to about 4 percent of the composition.

20. A method as in claim 19, wherein isopropyl alcohol is in an amount by weight of about 81 percent;

glycerin is in an amount by weight of about 3 percent;

triethanolamine salicylate is in an amount by weight of about 15 percent; and aloe vera is in an amount by weight of about 1 percent.

21. A method for relieving pain, the method comprising:

applying a liquid composition to the skin surrounding the painful area, the composition comprising:

alcohol in an amount by weight of about 60 to about 93 percent;

glycerin in an amount by weight of about 2 to about 14 percent;

an analgesic agent in an amount by weight of about 2 to about 28 percent, the analgesic agent comprising a derivative of salicylic acid; and aloe vera in an amount by weight of at least about 0.3 percent, the liquid composition permeating skin to relieve pain, and allowing the liquid composition to permeate the skin to relieve pain.

22. A method as in claim 21 wherein aloe vera is in an amount by weight of about 0.3 to about 4 percent of the composition.

23. A method as in claim 22, wherein the alcohol comprises isopropyl alcohol is in an amount by weight of about 87.9 to about 88.4 percent;

glycerin is in an amount by weight of about 4.8 percent;

the analgesic agent comprises acetylsalicylic acid in an amount by weight of about 5.7 percent to about 6.1 percent; and aloe vera is in an amount by weight of about 1.1 percent.

24. A method as in claim 22, wherein the alcohol comprises isopropyl alcohol in an amount by weight of about 81 percent;

glycerin is in an amount by weight of about 3 percent;

the analgesic agent comprises triethanolamine salicylate in an amount by weight of about 15 percent; and aloe vera is in an amount by weight of about 1 percent.

25. A method as in claim 21, wherein the step of applying the liquid composition to the skin is achieved by spraying the liquid composition on the skin.

26. A liquid composition applied transdermally for relief of pain, the composition comprising the reaction products of:

alcohol in an amount by weight of about 60 percent to about 93 percent;

glycerin in an amount by weight of about 2 to about 14 percent;

an analgesic agent in an amount by weight of about 2 to about 28 percent, the analgesic agent comprising a derivative of salicylic acid, and aloe vera in an amount by weight of at least about 0.3 percent, the liquid composition permeating skin to relieve pain.

27. A liquid composition as recited in claim 26, wherein the alcohol in an amount by weight of about 60 percent to about 93 percent is selected from the group consisting of ethyl alcohol and isopropyl alcohol.

28. A liquid composition as recited in claim 27, wherein the analgesic agent comprises a salicylate.

29. A liquid composition as recited in claim 26, wherein the analgesic agent comprises a salicylate.

* * * * *